United States Patent [19]

Sommer et al.

[11] Patent Number: 4,672,123

[45] Date of Patent: Jun. 9, 1987

[54] CHEMICAL AGENTS

[75] Inventors: Harold Z. Sommer, Havre de Grace; George E. Wicks, Jr., Baltimore, both of Md.

[73] Assignee: The United States of America as represented by the Secretary of the Army, Washington, D.C.

[21] Appl. No.: 636,574

[22] Filed: Apr. 28, 1967

[51] Int. Cl.[4] .......... C07D 213/65

[52] U.S. Cl. .......... 546/292; 102/367; 424/43; 514/890

[58] Field of Search .......... 260/294 A, 296; 167/46 A, 47; 424/263; 514/351, 890; 546/300, 292

[56] References Cited

U.S. PATENT DOCUMENTS 2,512,732 6/1950 Aeschlimann et al. .......... 546/300 X
2,857,390 10/1958 Kirchner .......... 260/294 A
3,188,955 6/1965 Brown .......... 102/24

*Primary Examiner*—Richard D. Lovering

*Attorney, Agent, or Firm*—Anthony T. Lane; Robert P. Gibson; Harold H. Card, Jr.

[57] ABSTRACT

New chemical compounds having the generic formula:

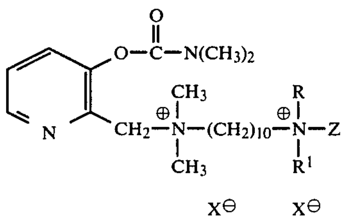

wherein X is one equivalent of an anion selected from monovalent and polyvalent anions, and R,R' and Z are aliphatic radicals selected from the group consisting of ethyl, propyl, and butyl, with the provision that when Z is a radical selected from the group of octyl, dodecyl, and cyclohexyl, R,R' are selected from methyl and ethyl groups, and having utility as incapacitating agents and in munitions.

3 Claims, No Drawings

CHEMICAL AGENTS

This invention relates to the synthesis of new toxic chemical compounds which are useful as chemical warfare agents. More particularly, our invention is concerned with novel compounds produced by means of a quaternizing reaction.

The chemical agent acts mostly on the peripheral cholinergic nervous system which includes the motor nerves, the preganglionic fibers, the ganglia, the postganglionic parasympathetic fibers, and neuromuscular functions. The transmission of impulses along a nerve or from nerve fibers to muscle fibers or secretory cells or from one nerve fiber to another across synapses in ganglia is thought to involve chemical changes either directly or as the source of potential differences.

Quaternary ammonium compounds in general are known to be physiologically active materials. Mainly because of their positively charged "onium" centers, they are attracted by anionic sites in animal tissues, particularly those situated at cell surfaces and interfaces. They can induce physiological responses that mimic or antagonize the action of acetylcholine as a result of their interaction with the various physiological receptor sites of acetylcholine, especially those at membranes of muscle cells. They also combine with enzymes such as acetylcholinesterase, other esterases, acetylcholineacetylase, etc., thus inhibiting their participation in the biological processes.

One of the significant anatomical differences between the neuromuscular junctions and other acetylcholine receptive sites is the absence of a membrane barrier or a sheath such as envelops the ganglia. The comparative ease of accessibility of the neuromuscular junctions to "onium" compound contributes to their relatively fast onset of action and partly explains why in many instances relatively small doses suffice to envoke physiological actions that modify or interrupt normal neuromuscular impulse transmission.

Depending on their chemical structures, different quaternary compounds interfere with the mechanism of impulse transmission in different manners and the final physiological effects can vary considerably. Some quaternary ammonium compounds are used as therapeutic agents, others are known to be lethal. The magnitude, accessibility, and distribution of the positive charges in quaternary compounds are believed to be the key factors in the determination of specificity of action. Recognition of these facts explains the strikingly different physiological behavior so often observed when structurally very closely related compounds are compared. The nature of the groups attached to the quaternary nitrogens influences the distribution of the cationic charges. The length and branching of aliphatic chains and the volume and configuration of aromatic and alicyclic rings have a bearing on the ease or difficulty of approach to the specific receptor sites. Electrophilic and nucleophilic centers in the molecule will insert their inductive effects on the positive charges and can also aid in the interaction with the "esteratic sites" of various enzymes. These sites are believed to be located in close vicinity to the anionic sites of the active centers. Substitution of different functional groups influence association and hydration and may considerably change the solubilities in physiological media. In bis-quaternary and poly-quaternary compounds, the electric charges must be considered. These factors contribute to govern the rate and reversibility of the chemical reactions involved, and contribute to determine the final physiological responses.

Our chemical agents interfere with the normal process of neuromuscular impulse transmission and thus disrupt the propagation of impulses from nerve to muscles. We have also found these compounds to be extremely toxic at relatively low dose levels in various animals.

The object of this invention is to synthesize new lethal agents useful in chemical warfare in high yields wherein said products are well suited for industrial scale manufacture.

Our compounds may be employed in any munition suitable for handling a relatively non-volatile toxic agent such as bombs, shells, spray tanks, rockets, missiles, aerosol generators, and others.

Other objects of and uses for the invention will in part be obvious and will in part appear hereinafter in the following detailed description thereof.

In accordance with our invention an aliphatic tertiary amine was quaternized with N-(10-bromodecyl)-N-(3-dimethylcarbamoxy-α-picolinyl) -N,N-dimethylammonium bromide under reflux conditions in a solvent such as acetonitrile, acetone, chloroform or a mixture of these solvents. Reflux was maintained for 24–60 hours. The solvent was evaporated, the oily residue mixed in a boiling aliphatic ketone such as acetone, and the ketone decanted. The remaining gummy material was dissolved in a solvent such as acetonitrile or methanol and the solution treated with decolorizing charcoal. The purified solution was concentrated to a few milliliters and the concentrate evaporated under reduced pressure. The solid material that remained constituted new compounds of the present invention which may be represented by the following generic formula:

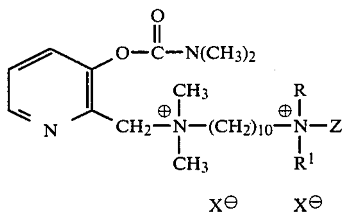

wherein X is one equivalent of a monovalent or polyvalent anion and R,R′, are lower alkyl radicals such as methyl, ethyl, propyl, butyl, and Z is an alkyl or cyclohexyl group, with the provision that when Z is of relatively higher molecular weight, such as octyl, dodecyl, or cyclohexyl, R,R′ are methyl or ethyl groups.

The procedure used for the preparation of the new toxic materials is schematically shown below:

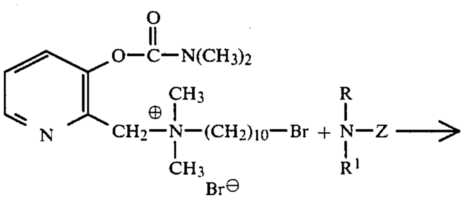

-continued

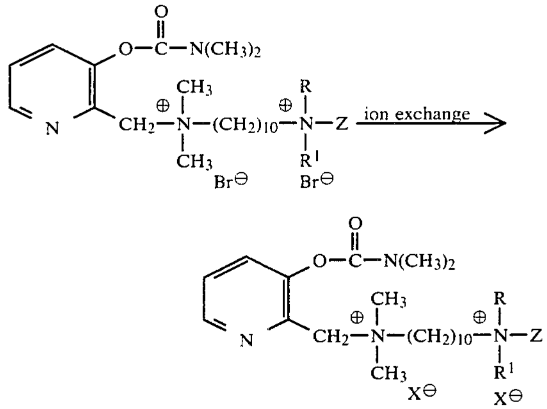

wherein X is a halide ion, preferably bromide and R,R' and Z as defined above.

If compounds are desired in which X is other than a halide ion, the above quaternary compounds are treated with the desired acid by simple exchange reactions as set forth below.

EXAMPLE 1

N-(10-bromodecyl)-N-(3-dimethylcarbamoxy-α-picolinyl)-N,N-dimethylammonium bromide (1.05 grams) and n-tributylamine (0.74 grams) were dissolved in an acetonitrile-chloroform mixture (1:3) and the solution refluxed for 48 hours. The solvent was then evaporated, the resultant oily and viscous material stirred in hot acetone, and the acetone decanted. The remaining gummy material was dissolved in methanol and treated with decolorizing charcoal. After the charcoal was removed by filtration, the filtrate was concentrated at normal pressure to a few milliliters and the concentrate placed for 4 hours in an apparatus which was kept under reduced pressure (1 mm) at 78° C. Thus, 0.5 grams of the product, 1-(N,N,N-tributylammonio)-10-[N-(3-dimethylcarbamoxy-α-picolinyl)-N,N-dimethylammonio]decane dibromide, was obtained as a white deliquescent solid. Because of its deliquescency, a sample of the compound was converted to and analyzed as the tetraphenylboronate salt. The dibromide salt was dissolved in water and to this solution an aqueous solution of sodium tetraphenyl boron (in molar excess) was added. The solid that formed was separated by filtration, washed a few times with water, and then dried.

Analysis for $C_{81}H_{104}B_2N_4O_2$: Calcd: C, 81.9; H, 8.8; N,4.7.Found: C, 81.9; H, 9.0; N,4.9.

| Toxicity IV, $LD_{50}$ | |
|---|---|
| Rabbits | Mice |
| 0.005 mg/kg | 0.028 mg/kg |

EXAMPLE 2

N-(10-bromodecyl)-N-(3-dimethylcarbamoxy-α-picolinyl)-N,N-dimethylammonium bromide (1.05 grams) and N,N-dimethylaminocyclohexane (0.65 grams) were dissolved in 10 ml of acetone and the solution refluxed for 24 hours. After the mixture was allowed to cool to room temperature, the solvent was decanted. The remaining viscous oil was stirred in about 50 ml of boiling acetone for 10 minutes after which time the acetone was decanted. The gummy residue was dissolved in methanol and treated with decolorizing charcoal. After the charcoal was removed by filtration, the filtrate was concentrated at atmospheric pressure to a few milliliters and the concentrate placed for 4 hours in an apparatus which was kept under reduced pressure (1 mm) at 78° C. Thus 0.9 grams of the product, 1-(N,N-dimethyl-N-cyclohexylammonio)-10-[N-(3-dimethylcarbamoxy-α-picolinyl)-N,N-dimethylammonio]decane dibromide, was obtained as a white solid.

Analysis for $C_{29}H_{54}BR_2N_4O_2$: Calcd: C, 53.5; H, 8.4; Br, 24.6.Found: C, 53.3; H, 8.5; Br, 24.2.

| Toxicity IV, $LD_{50}$ | |
|---|---|
| Rabbits | Mice |
| 0.010 mg/kg | 0.028 mg/kg |

Method of Preparation of N-(10-Bromodecyl)-N-(3-dimethylcarbamoxy-2-pyridylmethyl) dimethylammonium Bromide A solution of 62.3 grams of 2-dimethylaminomethyl-3-dimethyl-carbamoxypyridine and 251 grams of 1,10 dibromodecane was refluxed for 7 days in 1 liter of anhydrous ether. The product that formed was collected on a filter, washed with two 100 ml portions of anhydrous ether, and dissolved in 1 liter of acetone. The acetone solution was treated with decolorizing carbon and filtered. The filtrate was concentrated under reduced pressure to approximately 200 ml. Ether was added until the solution became turbid. The mixture was then seeded and chilled overnight. The resultant crystalline product was collected and further purified by recrystallization from ethyl acetate. The pure product was dried in vacuo for 2 hours, yielding 76 grams of material, m.p. 90° to 92° C.

Analysis for $C_{21}H_{37}Br_2N_3O_2$: Calculated : C, 48.2; H, 7.1; $Br^-$ (ionic), 15.3; O, 6.1. Found : C, 48.2; H, 7.0; $Br^-$ (*ionic*), 15.2; O, 6.2.

The compounds that are representative of our invention are listed below by name and chemical structure:

1-(N,N,N-triethylammonio)-10-[N-(3-dimethylcarbamoxy-α-picolinyl)-N,N-dimethylammonio]decane dibromide.

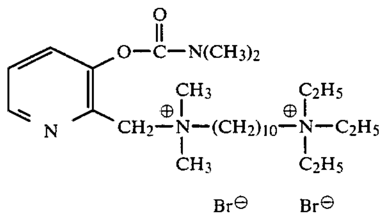

1-(N,N,N-tributylammonio)-10-[N-(3-dimethylcarbamoxy-α-picolinyl)-N,N-dimethylammonio]decane dibromide.

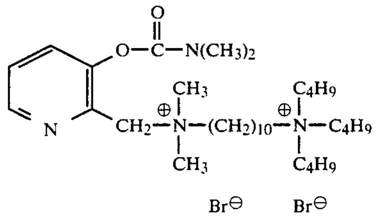

1-(N,N,N,-tripropylammonio)-10-[N-(3-dimethylcarbamoxy-α-picolinyl)-N,N-dimethylammonio]decane dibromide.

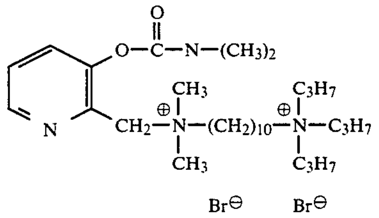

1-(N,N-dimethyl-N-octylammonio)-10-[N-(3-dimethylcarbamoxy-α-picolinyl)-N,N-dimethylammonio]-decane dibromide.

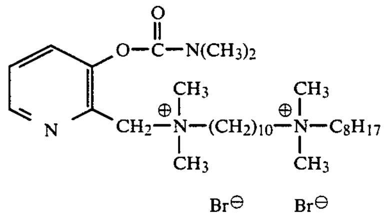

1-(N,N-dimethyl-N-dodecylammonio)-10-[N-(3-dimethylcarbamoxy-αpicolinyl)-N,N-dimethylammonio]decane dibromide.

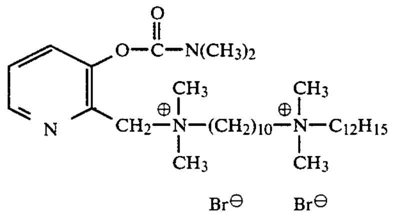

1-(N,N-dimethyl-N-cyclohexylammonio)-10-[N-(3-dimethylcarbamoxy-α-picolinyl)-N,N-dimethylammonio]decane dibromide.

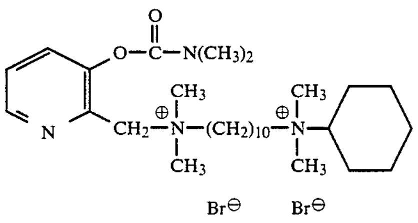

We have shown preferred compounds in which the anion is limited to the halogen moiety, in particular the bromide, because the bromoalkanes are good quaternizing agents. In general, however, it is only necessary that the anions merely have to meet the requirement of being capable of forming a stable salt with the quaternary nitrogen. Thus the halogen ions can be exchanged with other anions of relatively strong monovalent or polyvalent acids by conventional methods. For example, if $x^-$ is a bromide in the final product, a solution of the compound can be treated with a basic ion exchange resin or mixed with silver oxide and subsequently the desired acid is added to the quaternary hydroxide solution. Anions other than the halogen may also be obtained by metathesis with the halide form of quaternary ammonium compound. Suitable as representatives of $x^-$ are the anions hydrogen oxalate, perchlorate, nitrate, tetraphenylboronate, hydrogen sulfate. Representative examples of these additional end products are:

1-(N,N,N-tributylammonio)-10-[N-(3-dimethylcarbamoxy-α-picolinyl)-N,N-dimethylammonio]decane di(hydrogen oxalate).

1-(N,N,N-tributylammonio)-10-[N-(3-dimethylcarbamoxy-α-picolinyl)-N,N-dimethylammonio]decane diperchlorate.

1-(N,N,N-tributylammonio)-10-[N-(3-dimethylcarbamoxy-α-picolinyl)-N,N-dimethylammonio]decane dinitrate.

1-(N,N,N-tributylammonio)-10-[N-(3-dimethylcarbamoxy-α-picolinyl)-N,N-dimethylammonio]decane di(tetraphenylboronate).

1-(N,N,N-tributylammonio)-10-[N-(3-dimethylcarbamoxy-α-picolinyl)-N,N-dimethylammonio decane di(hydrogen sulfate).

We claim:

1. New chemical compounds having the generic formula:

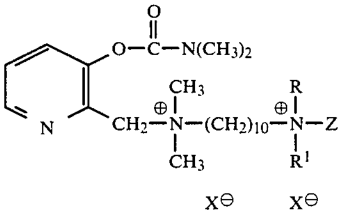

wherein X is one equivalent of an anion selected from monovalent and polyvalent anions, said anions being selected from the group consisting of halide, hydrogen oxalate, perchlorate, hydrogen sulfate, nitrate, and tetraphenylboronate, and R,R′ are lower alkyl radicals selected from the group consisting of methyl, ethyl, propyl, and butyl and Z is an alkyl or cyclohexyl group, with the provision that when Z is a radical selected from the group of octyl, dodecyl, and cyclohexyl, R,R′ are selected from methyl and ethyl groups.

2. New chemical compounds selected from the group of compounds having the names 1-(N,N,N-triethylammonio)-10-[N-(3-dimethylcarbamoxy-α-picolinyl)-N,N-dimethylammonio] decane dibromide; 1-(N,N,N-tributylammonio)-10-[N-(3-dimethylcarbamoxy-α-picolinyl)-N,N-dimethylammonio]decane dibromide; 1-(N,N-dimethyl-N-octylammonio)-10-[N-(3-dimethylcarbamoxy-α-picolinyl)-N,N-dimethylammonio]decane dibromide; and 1-(N,N-dimethyl-N-cyclohexylammonio)-10-[N-(3-dimethylcarbamoxy-α-picolinyl)-N,N-dimethylammonio]decane dibromide.

3. A method of producing a new chemical compound having the generic formula:

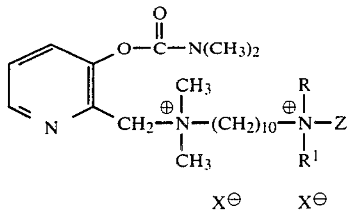

wherein X is a one equivalent of an anion selected from monovalent and polyvalent anions, said anions being selected from the group consisting of halide, hydrogen oxalate, perchlorate, hydrogen sulfate, nitrate, and tetraphenylboronate, and R,R′ are lower alkyl radicals selected from the group consisting of methyl, ethyl, propyl, and butyl and Z is an alkyl or cyclohexyl group, with the provision that when Z is a radical selected from the group of octyl, dodecyl, and cyclohexyl, R,R′ are selected from methyl and ethyl groups, comprising the steps of refluxing a solution of an aliphatic tertiary amine and N-(10-bromodecyl)-N-(3-dimethylcarbamoxy-α-picolinyl)-N,N,-dimethyl-ammonium X, wherein X is as described above, in solvent selected from the group consisting of acetonitrile, acetone, chloroform, and any mixture of these solvents; filtering the refluxed solution; washing the solid collected on the filter; dissolving the washed solid in acetone; treating the acetone-solid solution with decolorizing carbon; filtering the acetone-solid decolorizing carbon solution; concentrating the filtrate under reduced pressure; adding ether to the concentrated filtrate to produce turbidity; seeding the ether-concentrated-filtrate; chilling the seeded ether-concentrated filtrate; recrystallizing the product.

* * * * *